(12) United States Patent
Nishijima

(10) Patent No.: US 12,343,186 B2
(45) Date of Patent: Jul. 1, 2025

(54) X-RAY COMPUTED TOMOGRAPHY APPARATUS

(71) Applicant: Canon Medical Systems Corporation, Otawara (JP)

(72) Inventor: Akira Nishijima, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 242 days.

(21) Appl. No.: 18/158,492

(22) Filed: Jan. 24, 2023

(65) Prior Publication Data

US 2023/0233163 A1 Jul. 27, 2023

(30) Foreign Application Priority Data

Jan. 25, 2022 (JP) .................................. 2022-009670

(51) Int. Cl.
*A61B 6/40* (2024.01)
*A61B 6/42* (2024.01)

(52) U.S. Cl.
CPC .............. *A61B 6/40* (2013.01); *A61B 6/4208* (2013.01)

(58) Field of Classification Search
None
See application file for complete search history.

(56) References Cited

U.S. PATENT DOCUMENTS

2015/0055753 A1* 2/2015 Tajima ................. A61B 6/4283
378/62

FOREIGN PATENT DOCUMENTS

JP 2020-74825 A 5/2020

* cited by examiner

*Primary Examiner* — Edwin C Gunberg
(74) *Attorney, Agent, or Firm* — Oblon, McClelland, Maier & Neustadt, L.L.P.

(57) ABSTRACT

A tube voltage control circuitry switches a tube voltage applied to an X-ray tube between a first tube voltage and a second tube voltage of lower value than the first tube voltage. A first signal generating circuitry generates a first switching signal at a first time interval. A view switching circuitry switches a view based on the first switch signal. A data acquisition circuitry performs data acquisition for each view via an X-ray detector. A second signal generating circuitry generates a second switch signal at a second time interval shorter than the first time interval. A gain switching circuitry switches gains of the data acquisition circuitry based on the second switch signal.

13 Claims, 10 Drawing Sheets

X-RAY COMPUTED TOMOGRAPHY APPARATUS

CROSS-REFERENCE TO RELATED APPLICATION(S)

This application is based upon and claims the benefit of priority from Japanese Patent Application No. 2022-009670, filed Jan. 25, 2022, the entire contents of which are incorporated herein by reference.

FIELD

Embodiments described herein relate generally to an X-ray computed tomography apparatus.

BACKGROUND

As one of the imaging techniques performed by an X-ray computed tomography apparatus, there exists a technique called "dual energy scan" that performs imaging while switching between two types of tube voltages and then acquires two types of projection data corresponding to two types of energy. The technique of alternately switching tube voltages is called "kV switching". During kV switching, the gain of data acquisition circuitry is not switched, and data acquisition is performed at the same gain (amplification factor). Performance of kV switching at the same gain causes a signal-to-noise ratio (SN ratio) to degrade due to minimal gain on the low tube voltage side, while a large gain on the high tube voltage side triggers overflow and a likely artifact or a gap in CT values.

DETAILED DESCRIPTION

In general, according to one embodiment, an X-ray computed tomography apparatus includes tube voltage control circuitry, first signal generating circuitry, view switching circuitry, data acquisition circuitry, second signal generating circuitry, and gain switching circuitry. The tube voltage control circuitry switches a tube voltage applied to an X-ray tube between a first tube voltage and a second tube voltage of lower value than the first tube voltage. The first signal generating circuitry generates a first switch signal at a first time interval. The view switching circuitry switches a view based on the first switch signal. The data acquisition circuitry performs data acquisition in units of the view via an X-ray detector. The second signal generating circuitry generates a second switch signal at a second time interval shorter than the first time interval. The gain switching circuitry switches gains of the data acquisition circuitry based on the second switch signal.

Hereinafter, embodiments of an X-ray computed tomography apparatus will be described in detail with reference to the drawings. In the descriptions provided below, constituents having the same or almost the same functions will be denoted by the same reference symbols, and a repeat description of such constituents will be provided only where necessary. The same element in different drawings may have different dimensions and scales between the drawings.

The X-ray computed tomography apparatus (X-ray CT apparatus) according to the embodiments has various types such as a third-generation CT apparatus and a fourth-generation CT apparatus, any of which is applicable to the embodiments. The third-generation CT apparatus is of a "rotate/rotate-type", in which an X-ray tube and a detector integrally rotate about a subject. The fourth-generation CT apparatus is of a "stationary/rotate-type", in which a number of X-ray detection elements arrayed to form a ring shape are stationary and only an X-ray tube rotates about a subject. The X-ray computed tomography apparatus according to the embodiments is applicable to both a single-tube apparatus having a single pair of an X-ray tube and a detector mounted on a rotational ring and a multiple-tube apparatus having multiple pairs of an X-ray tube and a detector mounted on a rotational ring; however, only a single-tube apparatus will be described below.

First Embodiment

Figure 1:
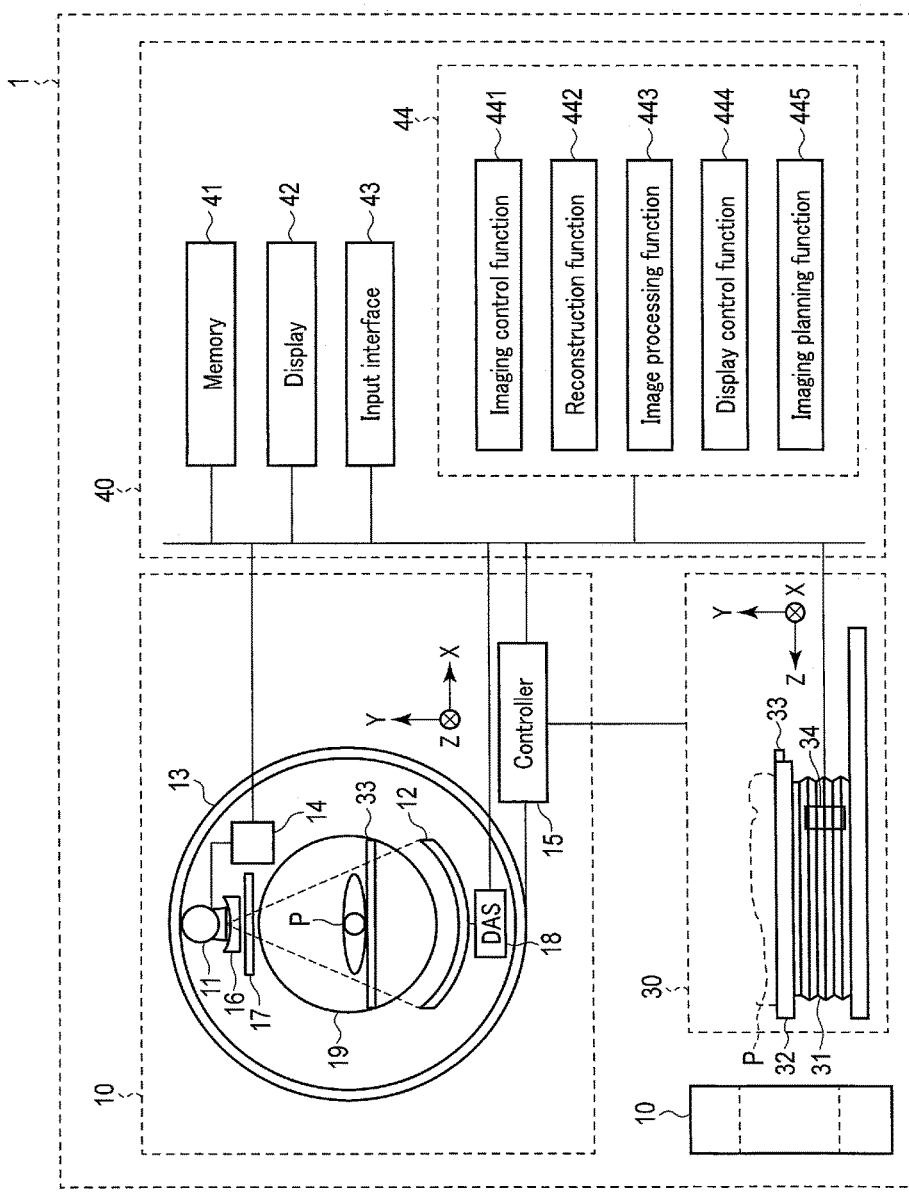
FIG. 1 is a diagram showing an example of a configuration of an X-ray computed tomography apparatus according to a first embodiment.

FIG. 1 is a diagram showing a configuration of an X-ray computed tomography apparatus 1 according to a first embodiment. The X-ray computed tomography apparatus 1 applies X-rays emitted from an X-ray tube 11 to a subject P and detects the emitted X-rays with an X-ray detector 12. The X-ray computed tomography apparatus 1 generates a CT image relating to the subject P based on output from the X-ray detector 12.

As shown in FIG. 1, the X-ray computed tomography apparatus 1 includes a gantry 10, a couch 30, and a console 40. For the convenience of explanation, FIG. 1 shows the gantry 10 in multiple areas; however, the number of gantries 10 installed in the X-ray computed tomography apparatus 1 may be one or more than one. The gantry 10 is a scanner which has a configuration for performing X-ray CT imaging on the subject P. The couch 30 is a carrier device on which the subject P to be subjected to X-ray CT imaging is placed and which regulates the position of the subject P. The console 40 is a computer that controls the gantry 10. For example, the gantry 10 and the couch 30 are installed in a CT examination room, and the console 40 is installed in a control room adjacent to the CT examination room. The gantry 10, the couch 30, and the console 40 are communicably connected to one another by wire or by radio. The console 40 need not necessarily be installed in the control room. For example, the console 40 may be installed together with the gantry 10 and the couch 30 in the same room. Alternatively, the console 40 may be incorporated into the gantry 10.

As shown in FIG. 1, the gantry 10 includes the X-ray tube 11, the X-ray detector 12, a rotational frame 13, an X-ray high voltage device 14, a controller 15, a wedge 16, a collimator 17, and data acquisition circuitry (data acquisition system; DAS) 18.

The X-ray tube 11 emits X-rays to the subject P. Specifically, the X-ray tube 11 includes a cathode that generates thermoelectrons, an anode that generates X-rays by receiving the thermoelectrons travelling from the cathode, and a vacuum tube that holds the cathode and the anode. The X-ray tube 11 is connected to the X-ray high voltage device 14 via a high voltage cable. The X-ray high voltage device 14 applies tube voltage between the cathode and the anode. Thermoelectrons travel from the cathode to the anode upon application of the tube voltage. Tube current flows as thermoelectrons travel from the cathode to the anode. As the X-ray high voltage device 14 applies high voltage and supplies filament current, thermoelectrons travel from the cathode (filament) to the anode (target) and collide with the anode, whereby X-rays are generated. Examples of the X-ray tube 11 include a rotating anode-type X-ray tube that generates X-rays by emitting thermoelectrons to the rotating anode.

The hardware to generate X-rays is not limited to the X-ray tube 11. For example, instead of the X-ray tube 11, a fifth-generation system may be used to generate X-rays. The fifth-generation system includes a focus coil that converges electron beams generated from an electron gun, a deflection coil that electromagnetically deflects the electron beams, and a target ring that surrounds a semiperimeter of the subject P and generates X-rays through collision of the deflected electron beams with the target ring.

The X-ray detector 12 detects the X-rays that have been emitted from the X-ray tube 11 and have passed through the subject P, and outputs an electric signal corresponding to the detected X-ray dose to the data acquisition circuitry 18. The X-ray detector 12 has a structure in which a plurality of X-ray detection element rows are aligned in a slice direction (row direction), with each of the X-ray detection element rows including a plurality of X-ray detection elements aligned in the channel direction. The X-ray detector 12 is, for example, an indirect conversion-type detector including a grid, a scintillator array, and an optical sensor array. The scintillator array includes a plurality of scintillators. The scintillator outputs an amount of light corresponding to an amount of incident X-rays. The grid is arranged on the X-ray incident surface side of the scintillator array, and includes an X-ray shielding plate that absorbs scattered X-rays. The grid may be referred to as a "collimator (one-dimensional collimator or two-dimensional collimator)". The optical sensor array converts the light to an electric signal corresponding to the amount of light output from the scintillator. For example, a photodiode is used as the optical sensor. The X-ray detector 12 may be a direct conversion-type detector.

The rotational frame 13 is an annular frame that supports the X-ray tube 11 and the X-ray detector 12 rotatably about a rotation axis (Z-axis). Specifically, the rotational frame 13 supports the X-ray tube 11 and the X-ray detector 12 so that the X-ray tube 11 and the X-ray detector 12 face each other. The rotational frame 13 is supported by a stationary frame (not shown) so as to be able to rotate about the rotation axis. The controller 15 causes the rotational frame 13 to rotate about the rotation axis, whereby the X-ray tube 11 and the X-ray detector 12 are rotated about the rotation axis. The rotational frame 13 rotates about the rotation axis at a predetermined angular velocity upon receiving power from a drive mechanism of the controller 15. A field of view (FOV) of an image is set at a bore 19 of the rotational frame 13.

In the embodiment, the rotation axis of the rotational frame 13 in a non-tilted state or the longitudinal direction of a top plate 33 of the couch 30 is defined as a "Z-axis direction"; the axial direction orthogonal to the Z-axis direction and horizontal to the floor is defined as an "X-axis direction"; and the axial direction orthogonal to the Z-axis direction and vertical to the floor is defined as a "Y-axis direction".

The X-ray high voltage device 14 includes a high-voltage generator and an X-ray controller. The high-voltage generator includes electric circuitry, such as a transformer and a rectifier, and generates high voltage to be applied to the X-ray tube 11 and filament current to be supplied to the X-ray tube 11. The X-ray controller controls output voltage according to the X-rays emitted by the X-ray tube 11. The high-voltage generator may adopt a transformer system or an inverter system. The X-ray high voltage device 14 may be provided either to the rotational frame 13 in the gantry 10 or to the stationary frame (not shown) in the gantry 10.

The wedge 16 adjusts the dose of X-rays emitted to the subject P. Specifically, the wedge 16 attenuates the X-rays so that the dose of X-rays emitted from the X-ray tube 11 to the subject P exhibits a predetermined distribution. For example, a metal plate made of aluminum or the like, such as a wedge filter or a bow-tie filter, is used as the wedge 16.

The collimator 17 limits the range of applying X-rays that have passed through the wedge 16. The collimator 17 slidably supports a plurality of lead plates that shield X-rays and adjusts the shape of slits formed by the lead plates. The collimator 17 may be referred to as an "X-ray diaphragm".

The data acquisition circuitry 18 reads from the X-ray detector 12 electric signals corresponding to the dose of X-rays detected by the X-ray detector 12. The data acquisition circuitry 18 amplifies the read electric signals and integrates them during a view period, thereby acquiring projection data with a digital value corresponding to the dose of X-rays during the view period. The data acquisition circuitry 18 is implemented by, for example, an application-specific integrated circuit (ASIC) equipped with a circuit element capable of generating projection data. The digital data is transmitted to the console 40 via a non-contact data transmitter or the like.

In the embodiment, an integrating-type X-ray detector 12 and an X-ray computed tomography apparatus 1 equipped with an integrating-type X-ray detector 12 are described as examples; however, the technique according to the embodiment is also applicable to a photon counting-type X-ray detector or an X-ray computed tomography apparatus equipped with a photon counting-type X-ray detector.

The controller 15 controls the X-ray high voltage device 14 or the data acquisition circuitry 18 to perform X-ray CT imaging according to an imaging control function 441 of processing circuitry 44 of the console 40. The controller 15 includes processing circuitry including a central processing unit (CPU), a micro processing unit (MPU), or the like and a drive mechanism such as a motor or an actuator. The processing circuitry includes, as hardware resources, a processor (such as a CPU) and a memory (such as a read only memory (ROM) or a random access memory (RAM)). The controller 15 may be implemented by an ASIC or a field programmable gate array (FPGA). Alternatively, the controller 15 may be implemented by another complex programmable logic device (CPLD) or a simple programmable logic device (SPLD). The controller 15 functions to control the operation of the gantry 10 and the couch 30 upon receipt of an input signal from an input interface 43 (described later) which is provided to the console 40 or the gantry 10. For example, the controller 15 performs control to rotate the rotational frame 13, control to tilt the gantry 10, and control to operate the couch 30 and the top plate 33 in response to an input signal. The control to tilt the gantry 10 is implemented by the controller 15 rotating the rotational frame 13 about an axis parallel to the X-axis direction based on tilt angle information input through the input interface provided to the gantry 10. The controller 15 may be provided in the gantry 10 or in the console 40.

The couch 30 includes a base 31, a support frame 32, the top plate 33, and a couch drive 34. The base 31 is provided on the floor. The base 31 is a housing that supports the support frame 32 movably in a direction perpendicular to the floor (i.e., the Y-axis direction). The support frame 32 is a frame provided on top of the base 31. The support frame 32 supports the top plate 33 slidably along the rotation axis (i.e., the Z-axis). The top plate 33 is a flexible plate on which the subject P is placed.

The couch drive 34 is housed in the housing of the couch 30. The couch drive 34 is a motor or actuator that generates power to move the support frame 32 and the top plate 33 on which the subject P is placed. The couch drive 34 operates according to the control performed by the console 40 or the like.

The console 40 includes a memory 41, a display 42, an input interface 43, and processing circuitry 44. Data communication among the memory 41, the display 42, the input interface 43, and the processing circuitry 44 is performed via a bus. The console 40 is described as being separate from the gantry 10; however, the console 40 or some of the components of the console 40 may be included in the gantry 10.

The memory 41 is a storage device such as a hard disk drive (HDD), a solid state drive (SSD), or an integrated circuit storage device, which stores various types of information. The memory 41 stores, for example, projection data and reconstructed image data. Other than being a HDD, a SSD, or the like, the memory 41 may be a portable storage medium such as a compact disc (CD), a digital versatile disc (DVD), or a flash memory. Alternatively, the memory 41 may be a drive that reads and writes various types of information from and in, for example, a semiconductor memory device such as a flash memory or a random access memory (RAM). Alternately, a storage area of the memory 41 may be in the X-ray computed tomography apparatus 1, or in an external storage device connected over a network. The memory 41 stores a database described later.

The display 42 displays various types of information. For example, the display 42 outputs a medical image (CT image) generated by the processing circuitry 44, a graphical user interface (GUI) for receiving various operations from an operator, and the like. Various types of displays may be discretionarily and suitably adopted as the display 42. For example, a liquid crystal display (LCD), a cathode ray tube (CRT) display, an organic electro luminescence display (OELD), or a plasma display can be used as the display 42. The display 42 may be provided to the gantry 10. Also, the display 42 may be a desktop-type display, or be configured by a tablet terminal or the like capable of performing wireless communication with the main body of the console 40.

The input interface 43 receives various input operations from an operator which it converts into electric signals for outputting to the processing circuitry 44. For example, the input interface 43 receives, from an operator, acquisition conditions for acquiring projection data, reconstruction conditions for reconstructing CT images, image-processing conditions for generating post-processed images from the CT images, and the like. For example, a mouse, a keyboard, a trackball, a switch, a button, a joystick, a touch pad, a touch panel display, or the like can be suitably used as the input interface 43. In the embodiment, the input interface 43 does not necessarily include physical operation components such as a mouse, a keyboard, a trackball, a switch, a button, a joystick, a touch pad, and a touch panel display. Examples of the input interface 43 include processing circuitry for electric signals, which receives an electric signal corresponding to an input operation from an external input device separate from its own apparatus, and outputs this electric signal to the processing circuitry 44. The input interface 43 may be provided to the gantry 10. Alternatively, the input interface 43 may be constituted by, for example, a tablet terminal capable of performing wireless communication with the main body of the console 40.

The processing circuitry 44 controls the entire operation of the X-ray computed tomography apparatus 1 according to the electric signal of the input operation output from the input interface 43. The processing circuitry 44 generates image data based on the electric signal output from the X-ray detector 12. For example, the processing circuitry 44 includes a processor, such as a CPU, an MPU, or a GPU, and a memory, such as a ROM or a RAM, as hardware resources. With a processor that executes a program loaded into the memory, the processing circuitry 44 performs an imaging control function 441, a reconstruction function 442, an image processing function 443, a display control function 444, an imaging planning function 445, and the like. The functions 441 to 445 are each not limited to those implemented by single processing circuitry. Processing circuitry may be configured by combining a plurality of independent processors, and each of the processors may execute a program to implement the functions 441 to 445.

With the imaging control function 441, the processing circuitry 44 controls the X-ray high voltage device 14, the controller 15, and the data acquisition circuitry 18 in order to perform dual energy scan on the subject P.

With the reconstruction function 442, the processing circuitry 44 generates, for example, a dual energy CT (DECT) image such as a virtual monochromatic X-ray image or a material discrimination image based on the projection data resulting from application of high tube voltage and the projection data resulting from application of low tube voltage that are output from the data acquisition circuitry 18.

With the image processing function 443, the processing circuitry 44 converts the DECT image to a cross-sectional image of any cross section or a rendering image in any direction of a viewpoint. The conversion is performed based on an input operation received from an operator through the input interface 43. For example, the processing circuitry 44 performs three-dimensional image processing, such as volume rendering, surface volume rendering, image value projection processing, multi-planer reconstruction (MPR) processing, or curved MPR (CPR) processing, on the DECT image, and thereby generates rendering image data in any direction of a viewpoint. The generation of a rendering image in any direction of a viewpoint may be performed by the reconstruction function 442.

With the display control function 444, the processing circuitry 44 causes the display 42 to display various images generated by the image processing function 443. The images displayed on the display 42 include a DECT image, a cross-sectional image of any cross section, a rendering image in any direction of a viewpoint, and the like. The images displayed on the display 42 include an image for displaying an operation screen.

With the imaging planning function 445, the processing circuitry 44 sets an imaging plan relating to dual energy scan.

Hereinafter, the kV switching of the X-ray computed tomography apparatus 1 according to the embodiment will be described in detail.

Figure 2:
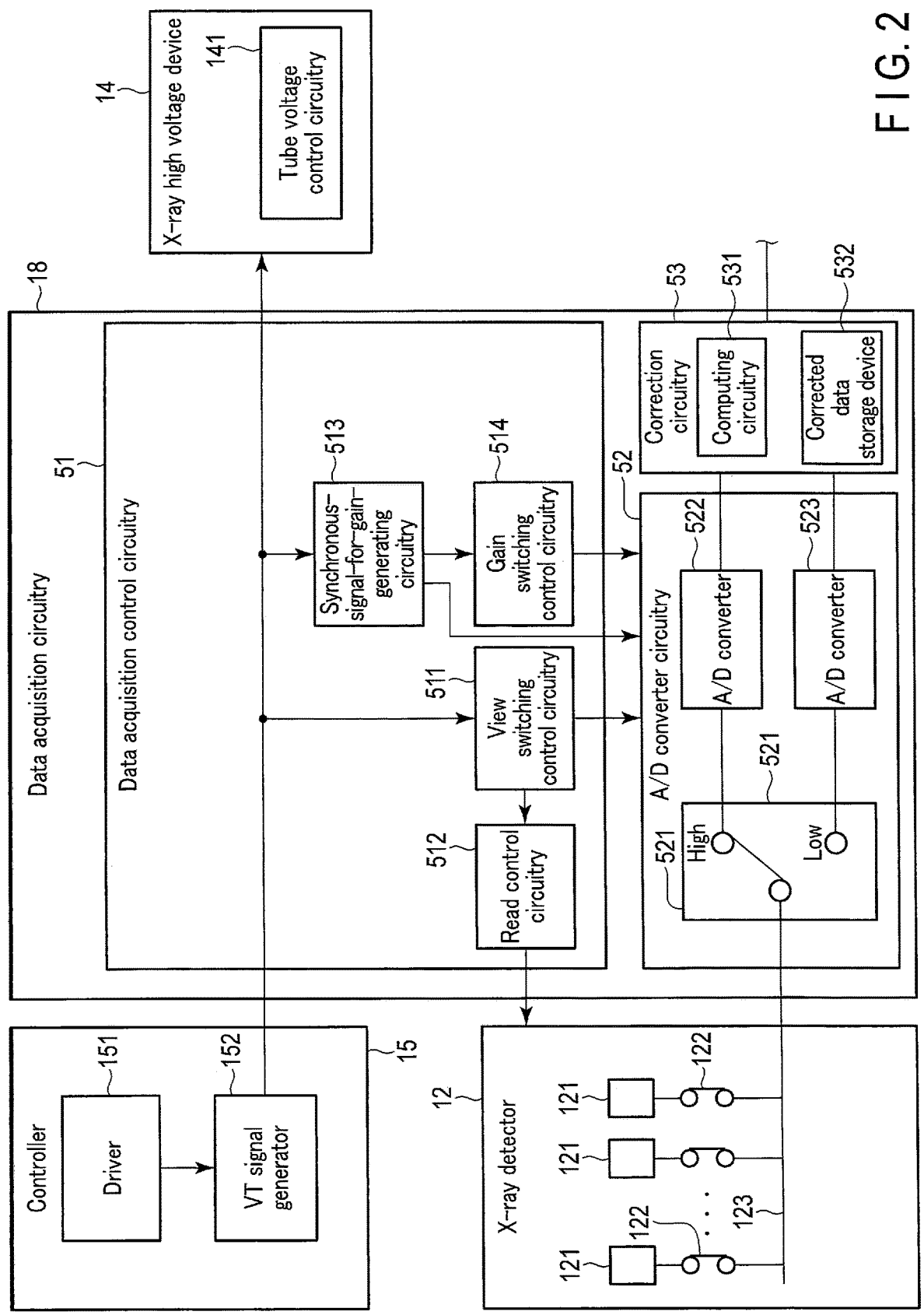
FIG. 2 is a diagram showing an example of configurations of main components relating to kV switching according to the first embodiment.

FIG. 2 is a diagram showing an example of main component configurations relating to kV switching according to the first embodiment. As shown in FIG. 2, the X-ray computed tomography apparatus 1 includes the X-ray detector 12, the X-ray high voltage device 14, the controller 15, and the data acquisition circuitry 18 as main components relating to kV switching.

As shown in FIG. 2, the X-ray detector 12 includes a plurality of X-ray detection elements 121. Each of the X-ray detection elements 121 includes a scintillator which outputs an amount of light corresponding to an amount of incident X-rays and an optical sensor which converts the light to an electric signal corresponding to the amount of light output from the scintillator. Each of the X-ray detection elements 121 is connected to a plurality of read switches 122 and to the data acquisition circuitry 18 via a read line 123.

The read switch 122 is a switching element that is driven based on a read control signal from read control circuitry 512. For example, a metal oxide semiconductor field effect transistor (MOS-FET) or the like may be used as the read switch 122. In response to an OFF signal, the read switches 122 open, and the reading of electric signals from the X-ray detection elements 121 is blocked. While the read switches 122 are open, the X-ray detection elements 121 receive incident X-rays to store electric signals. In response to an ON signal, the read switches 122 close, and the electric signals (electric charge signals) stored in the X-ray detection elements 121 are read.

Figure 3:
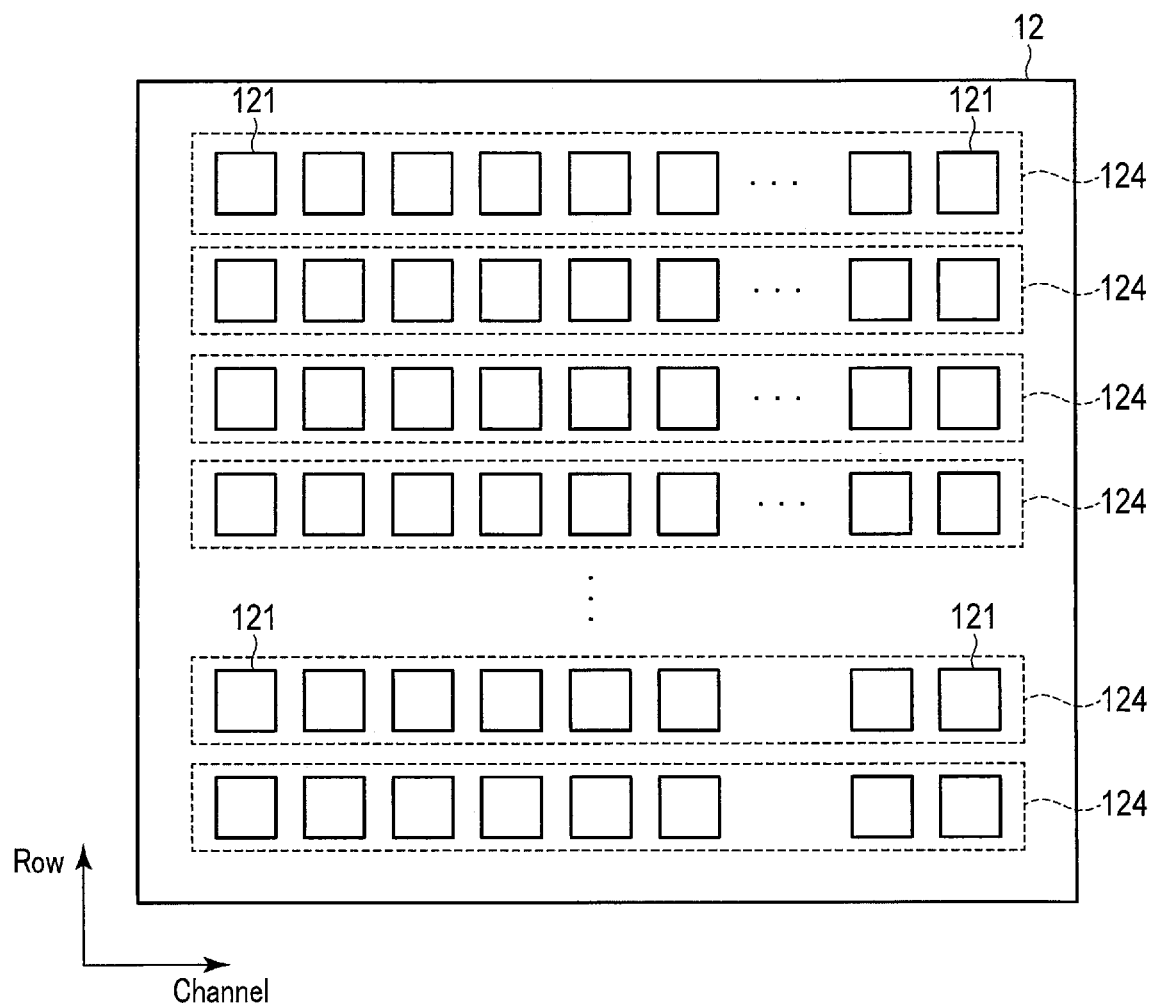
FIG. 3 is a plan view showing an array of X-ray detection elements.

FIG. 3 is a plan view showing an array of the X-ray detection elements 121. As shown in FIG. 3, a plurality of X-ray detection elements 121 are arrayed on the X-ray incident surface of the X-ray detector 12 two-dimensionally with respect to the row direction and the channel direction. The row direction is defined by a Z-axis direction parallel to the central axis of the bore, and the channel direction is defined by a rotational direction of the rotational frame 13. A plurality of X-ray detection element rows 124 are arrayed with respect to the row direction.

Electric signals are read from the X-ray detector 12 according to the embodiment by a sequential read method. In the sequential read method, reading of an electric signal is performed for each X-ray detection element row 124 with the times shifted from each other. For example, reading of an electric signal is performed in the order from the X-ray detection element row 124 in the first row to the X-ray detection element row 124 in the last row with the reading start time temporally shifted.

The controller 15 includes a driver 151 and a VT signal generator 152, as shown in FIG. 2. The driver 151 includes an actuator, such as a motor, and a power transmission mechanism, such as a belt for transmitting the power generated by the motor. The driver 151 rotates the rotational frame 13 about a rotation axis (Z-axis) at a predetermined angular velocity according to a control signal from the console 40.

The VT signal generator 152 generates a first switch signal at a first time interval. Specifically, the VT signal generator 152 generates the first switch signal, which is an electric pulse signal, for each of the first time intervals corresponding to the time interval at which the rotational frame 13 rotates at a predetermined angle. For example, the VT signal generator 152 is implemented by a rotary encoder installed in the driver 151. The first switch signal is a control signal used to switch views and will be hereinafter referred to as a "VT signal". The waveform of the VT signal is not particularly limited, but in the embodiment it is rectangular. The generated VT signal is output to the data acquisition circuitry 18. The VT signal generator 152 is an example of a first signal generator.

As shown in FIG. 2, the X-ray high voltage device 14 includes tube voltage control circuitry 141. The tube voltage control circuitry 141 alternately switches the tube voltage applied to the X-ray tube 11 between a high tube voltage and a low tube voltage. The tube voltage control circuitry 141 according to the first embodiment alternately switches the tube voltage between a high tube voltage and a low tube voltage based on the VT signal from the VT signal generator 152. The tube voltage control circuitry 141 is an example of a tube voltage controller.

As shown in FIG. 2, the data acquisition circuitry 18 includes data acquisition control circuitry 51, A/D converter circuitry 52, and correction circuitry 53.

The data acquisition control circuitry 51 is implemented by control circuitry such as FPGA and controls the reading of electric signals from the X-ray detector 12 and the data acquisition performed by the A/D converter circuitry 52. Specifically, the data acquisition control circuitry 51 includes view switching control circuitry 511, read control circuitry 512, synchronous-signal-for-gain-generating circuitry 513, and gain switching control circuitry 514. The view switching control circuitry 511, the read control circuitry 512, the synchronous-signal-for-gain-generating circuitry 513, and the gain switching control circuitry 514 may be mounted either in the form of hardware on separate control substrates or on a single control substrate.

The view switching control circuitry 511 switches views based on the VT signal. The view corresponds to a sampling period of digital data by the A/D converter circuitry 52. To give an example, the time period for the rotational frame 13 to navigate one round is divided into multiple views such as 1000 views or 2000 views. View numbers are added one by one as the view is switched. The view switching control circuitry 511 controls the read control circuitry 512 and the A/D converter circuitry 52 according to the switching of the view. The view switching control circuitry 511 is an example of a view switching unit.

The read control circuitry 512 controls the opening and closing of each of the read switches 122 connected to each of the X-ray detection elements 121 in the sequential read method. Specifically, the read control circuitry 512 controls the opening and closing of the read switches 122 so that reading from all the X-ray detection element rows is completed, while shifting the timing of starting reading electric signals for each X-ray detection element row 124. When the read switches 122 are to be closed, an ON signal is supplied, and when the read switches 122 are to be opened, an OFF signal is supplied.

The synchronous-signal-for-gain-generating circuitry 513 generates a second switch signal at a second time interval (high frequency) shorter than the first time interval of the VT signal. The second switch signal is referred to as a "synchronous signal for gain" since it is used for a synchronous signal for switching the gain of the A/D converter circuitry 52 (hereinafter referred to as "DAS gain"). To give an example, the synchronous signal for gain has a pulse generation cycle both synchronized with a VT signal and equal to the integral multiple of the pulse generation cycle of the VT signal. The method of generating a synchronous signal for gain is not particularly limited; however, a synchronous signal for gain may be generated by, for example, upsampling the VT signal. The synchronous signal for gain is supplied to the gain switching control circuitry 514 and the A/D converter circuitry 52. The synchronous-signal-for-gain-generating circuitry 513 is an example of a second signal generator.

The gain switching control circuitry 514 switches the DAS gain of the A/D converter circuitry 52 based on the synchronous signal for gain. Specifically, the gain switching control circuitry 514 switches the DAS gain between a DAS gain corresponding to a high tube voltage (hereinafter referred to as a "high-tube-voltage gain") and a DAS gain corresponding to a low tube voltage (hereinafter referred to as a "low-tube-voltage gain"). The gain switching control circuitry 514 switches the DAS gain between a high-tube-voltage gain and a low-tube-voltage gain so as to match the tube voltage corresponding to the digital data acquired via the X-ray detector 12. Specifically, when the DAS gain is switched to a high-tube-voltage gain, a high-gain switch signal is supplied, and when the DAS gain is switched to a low-tube-voltage gain, a low-gain switch signal is supplied. The gain switching control circuitry 514 is an example of a gain switching unit.

The A/D converter circuitry 52 acquires data for each view via the X-ray detector 12. Specifically, the A/D converter circuitry 52 converts an electric signal read from the X-ray detector 12 into digital data for each view at a high-tube-voltage gain or a low-tube-voltage gain under the control of the view switching control circuitry 511 and the gain switching control circuitry 514. The A/D converter circuitry 52 performs A/D conversion at a high-tube-voltage gain on an electric signal generated upon reception of X-rays emitted when a high tube voltage is applied, and performs A/D conversion at a low-tube-voltage gain on an electric signal generated upon reception of X-rays emitted when a low tube voltage is applied. Specifically, the A/D converter circuitry 52 includes a gain switching unit 521, an A/D converter 522 for high tube voltage, and an A/D converter 523 for low tube voltage. The A/D converter circuitry 52 is an example of data acquisition unit.

The gain switching unit 521 is arranged in a stage prior to the A/D converter 522 for high tube voltage and the A/D converter 523 for low tube voltage, and switches the DAS gain between a high-tube-voltage gain and a low-tube-voltage gain under the switching control executed by the gain switching control circuitry 514. Specifically, the stage following the gain switching unit 521 is branched into an A/D conversion system for high-tube-voltage gain and an A/D conversion system for low-tube-voltage gain. For example, the gain switching unit 521 includes a switch such as a three-point switch. The A/D converter 522 which amplifies an electric signal at a high-tube-voltage gain and converts the amplified electric signal into digital data is connected to one of the output terminals, and the A/D converter 523 which amplifies an electric signal at a low-tube-voltage gain and converts the amplified electric signal into digital data is connected to the other of the output terminals. In response to a high-gain switch signal, the three-point switch connects an input terminal and one of the output terminals, and an electric signal read from the X-ray detector 12 is supplied to the A/D converter 522 for high tube voltage. In response to a low gain switch signal, the three-point switch connects an input terminal and the other of the output terminals, and an electric signal read from the X-ray detector 12 is supplied to the A/D converter 523 for low tube voltage.

The A/D converter 522 for high tube voltage is an A/D converter which converts an electric signal into digital data at a high-tube-voltage gain. Specifically, the A/D converter 522 for high tube voltage performs A/D conversion at a high-tube-voltage gain on electric signals supplied from the X-ray detection elements 121 while the read switches 122 are closed in a first view corresponding to the time of scanning the subject P and applying a high tube voltage (hereinafter referred to as a "high-tube-voltage view"), and converts the electric signals into digital data. The digital data is referred to as "projection data for high tube voltage". The projection data is digital data subjected to image reconstruction.

The A/D converter 522 for high tube voltage performs A/D conversion at a high-tube-voltage gain on electric signals generated while the read switches 122 are open in the high-tube-voltage view, and converts the electric signals into digital data. The digital data is referred to as "drift-corrected data at high-tube-voltage gain". The drift-corrected data is digital data representing a temporal variation of a digital value associated with a change in the characteristics of the A/D converter circuitry 52 at the time of scanning. Correction of this temporal variation occurring in projection data is referred to as "drift correction". The drift-corrected data is used to perform drift correction on projection data. The A/D converter 522 also performs A/D conversion at a high-tube-voltage gain on electric signals read from the X-ray detection elements 121 while the read switches 122 are closed outside the time of scanning the subject P and at the time of applying a high tube voltage, and converts the electric signals into digital data. The digital data is referred to as "offset-corrected data at high-tube-voltage gain". The offset-corrected data is digital data representing a temporal variation of a digital value associated with a change in characteristics of the A/D converter circuitry 52 associated with individual variability, aging degradation, etc. Correction of this temporal variation occurring in projection data is referred to as "offset correction". The offset-corrected data is used to perform offset correction on projection data.

The A/D converter 523 for low tube voltage is an A/D converter which converts an electric signal into digital data at a low-tube-voltage gain. Specifically, the A/D converter 523 for low tube voltage performs A/D conversion at a low-tube-voltage gain on electric signals supplied from the X-ray detection elements 121 while the read switches 122 are closed in a second view corresponding to the time of scanning the subject P and applying a low tube voltage (hereinafter referred to as a "low-tube-voltage view"), and converts the electric signals into digital data. The digital data is referred to as "projection data for low tube voltage".

The A/D converter 523 for low tube voltage performs A/D conversion at a low-tube-voltage gain on electric signals generated while the read switches 122 are closed in the low-tube-voltage view, and converts the electric signals into digital data. The digital data is referred to as "drift-corrected data at low-tube-voltage gain". The A/D converter 523 for low tube voltage also performs A/D conversion at a low-tube-voltage gain on electric signals read from the X-ray detection elements 121 while the read switches 122 are closed outside the time of scanning the subject P and at the time of applying a low tube voltage, and converts the electric signals into digital data. The digital data is referred to as "offset-corrected data at low-tube-voltage gain".

The correction circuitry 53 is a processor that includes computing circuitry 531 and corrected data storage device 532. The computing circuitry 531 performs various kinds of data computing based on various kinds of digital data. To give an example, the computing circuitry 531 performs drift correction on projection data in a high-tube-voltage view based on the drift-corrected data at high-tube-voltage gain, and performs drift correction on projection data in a low-tube-voltage view based on drift-corrected data at low-tube-voltage gain. To give another example, the computing circuitry 531 performs offset correction on projection data in a high-tube-voltage view based on the offset-corrected data at high-tube-voltage gain, and performs offset correction on projection data in a low-tube-voltage view based on offset-corrected data at low-tube-voltage gain. The projection data for high tube voltage and the projection data for low tube voltage subjected to various corrections are supplied to the console 40 via a data transmission device, etc. The drift correction and offset correction need not be performed by the data acquisition circuitry 18, but may be performed by, for example, the processing circuitry 44 of the console 40.

The corrected data storage device 532 stores drift-corrected data at high-tube-voltage gain, offset-corrected data at high-tube-voltage gain, drift-corrected data at low-tube-voltage gain, and offset-corrected data at low-tube-voltage gain.

Next, an example of an operation of main components related to kV switching of the X-ray computed tomography apparatus 1 shown in FIG. 1 will be described. For the sake of illustration, the number of X-ray detection element rows is set to 320 rows.

Figure 4:
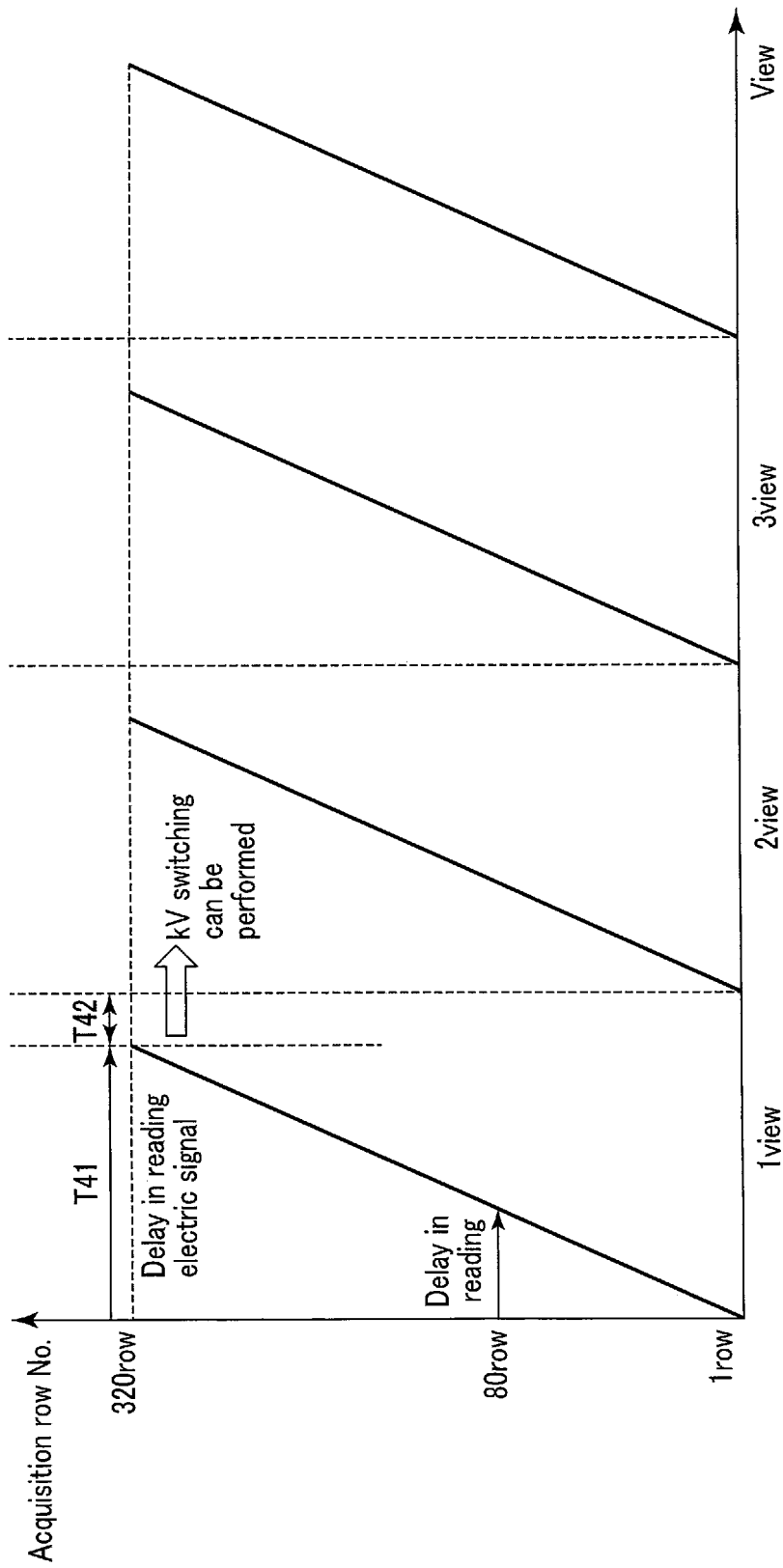
FIG. 4 is a diagram showing the time at which the reading of an electric signal of each X-ray detection element row is completed.

FIG. 4 is a diagram showing the time at which the reading of an electric signal from each X-ray detection element row is completed. The vertical axis of FIG. 4 represents the number of each X-ray detection element row (acquisition row No.), and the horizontal axis of FIG. 4 represents a view. The oblique solid line shown in FIG. 4 represents a line connecting the time at which the reading of an electric signal from each X-ray detection element row is performed. The reading of an electric signal from each X-ray detection element row is performed instantaneously. That is, the oblique solid line represents the time at which the reading of an electric signal from each X-ray detection element row is completed. In FIG. 4, the reading of an electric signal is performed in the order from the X-ray detection element row with row No. "1" to the X-ray detection element row with row No. "320". For example, in the X-ray detection elements 121 belonging to the starting row "1", storage (integration) of electric signals is performed commencing from the start time of each view, reading is performed instantaneously at the end time of the view, and the storage of electric signals is performed again commencing from the start time of the next view. In the sequential read method, the timing of starting reading is shifted for each X-ray detection element row, as shown in FIG. 4. Thus, in the X-ray detection element rows other than the starting row "1", the start time of each view does not coincide with the time at which reading is performed, causing a delay in reading electric signals. The farther the X-ray detection element row from the starting row "1", the greater the delay in the time at which an electric signal is read with respect to the time at which reading is performed in the starting row "1" (i.e., the starting time of the view); that is, the greater the gap between the time at which an electric signal is read and the time at which reading is performed in the starting row "1". In the final row "320", the time at which an electric signal is read is delayed by a period T41 with respect to the time at which reading is performed in the starting row "1".

In each view, tube voltage switching is prohibited until reading from the X-ray detection element row in the final row "320" is completed. Thus, tube voltage switching is permitted only in a period T42 starting from the time at which the reading from the X-ray detection element row in the final row "320" is performed to the start time of the next view.

Figure 5:
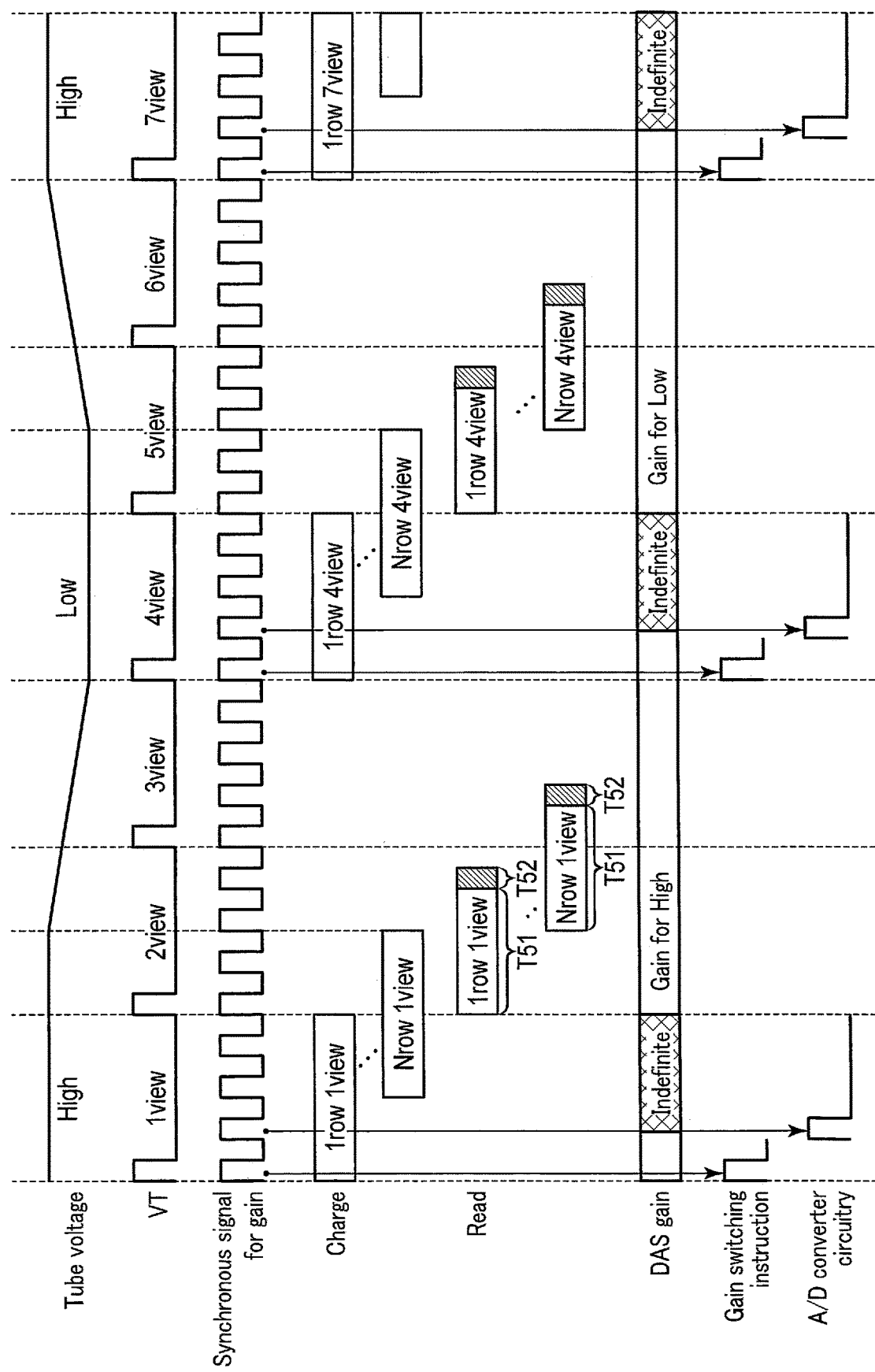
FIG. 5 is a diagram showing an example of a timing chart relating to the switching between a high tube voltage gain and a low tube voltage gain according to the first embodiment.

Next, switching between a high-tube-voltage gain and a low-tube-voltage gain according to the first embodiment will be described. FIG. 5 is a diagram showing an example of a timing chart related to the switching between a high tube voltage gain and a low tube voltage gain according to the first embodiment. There are N X-ray detection element row(s).

As shown in FIG. 5, a VT signal is repeatedly output by the VT signal generator 152 at a fixed first time interval, and the view is switched by the view switching control circuitry 511 when the VT signal is output. Tube voltage (kV) is alternately switched between a high tube voltage and a low tube voltage for each view by the X-ray high voltage device 14. In reality, a switch between a high tube voltage and a low tube voltage does not occur instantaneously, and a transitional period corresponding to about several views occurs. In FIG. 5, a stable period in which a voltage value is stable is set to 1.5 view, and a transitional period of tube voltage is also set to 1.5 view.

As shown in FIG. 5, a synchronous signal for gain is repeatedly output by the circuitry 513 at a second time interval, which is shorter than the first time interval, for generating a synchronous signal for gain in synchronization with the VT signal. The synchronous signal for gain is supplied to the gain switching control circuitry 514 and the A/D converter circuitry 52. The gain switching control circuitry 514 alternately switches a DAS gain between a high-tube-voltage gain and a low-tube-voltage gain based on the synchronous signal for gain. More specifically, the gain switching control circuitry 514 notifies the A/D converter circuitry 52 of a gain switch instruction in synchronization with a first pulse of the synchronous signal for gain in the stable period. As a gain switch instruction, a high-gain switch signal is supplied to the A/D converter circuitry 52 when the DAS gain is to be switched to a high-tube-voltage gain, and a low-gain switch signal is supplied to the A/D converter circuitry 52 when the DAS gain is to be switched to a low-tube-voltage gain.

There are various examples of gain change plan implementation relating to the question of whether to switch to a high-tube-voltage gain or low-tube-voltage gain. To give an example, by implementing the imaging planning function 445, the processing circuitry 44 creates, at the time of planning a scan, a list in which the type of DAS gain is set to the view number in advance (hereinafter referred to as a "gain switching plan"), as in a low-tube-voltage gain for the first view and a high-tube-voltage gain for the fourth view, for example. Before a scan is performed, the gain switching plan is supplied to the gain switching control circuitry 514. At the time when a scan is performed, the gain switching control circuitry 514 applies the current view number to the gain switching plan and specifies the type of DAS gain corresponding to the current view number, and then notifies the A/D converter circuitry 52 of the gain switch instruction for switching to the specified type. The current view number may be reported from the view switching control circuitry 511.

To give another example, a gain switch instruction may be transmitted from the processing circuitry 44 of the console 40 to the gain switching control circuitry 514 in real time during a scan. More specifically, the processing circuitry 44 applies the current view number to the gain switching plan and specifies the type of DAS gain corresponding to the current view number, and then transmits the gain switch instruction for switching to the specified type to the gain switching control circuitry 514. At this time, the processing circuitry 44 may transmit the gain switch instruction in synchronization with the VT signal. The gain switching control circuitry 514 may notify the A/D converter circuitry 52 of the same gain switch instruction as the gain switch instruction from the processing circuitry 44 in a switch instruction view for the current view.

The gain switching plan is described as being a list in which the type of DAS gain is set for each view number; however, the embodiment is not limited thereto. For example, if the type of DAS gain differs between an odd view number and an even view number, the gain switching plan may be a list in which the type of DAS gain is set for each of the odd view number and the even view number. Also, the gain switching plan may be represented by a relational expression of the view number and the type of DAS gain.

As described above, if the gain switch instruction is given in the first pulse of the synchronous signal for gain, the gain switching unit 521 of the A/D converter circuitry 52 switches the DAS gain in synchronization with the second pulse that follows the first pulse.

Specifically, in the stable period of the low tube voltage (such as the fourth view in FIG. 5), the gain switching control circuitry 514 notifies the A/D converter circuitry 52 of the gain switch instruction for switching to the low-tube-voltage gain in synchronization with the first pulse of the synchronous signal for gain. The gain switching unit 521 then switches the gain from the high-tube-voltage gain to the low-tube-voltage gain in synchronization with the second pulse that follows the first pulse. Since the operation of the A/D converter 523 for low tube voltage is unstable immediately after the DAS gain is switched, the period from the time when the DAS gain is switched to the starting time of the next view is used for stabilization of the A/D converter 523 for low tube voltage.

Likewise, in the stable period of the high tube voltage (such as the first view or the seventh view in FIG. 5), the gain switching control circuitry 514 notifies the A/D converter circuitry 52 of the gain switch instruction for switching to the high-tube-voltage gain in synchronization with the first pulse of the synchronous signal for gain. The gain switching unit 521 then switches the gain from the low-tube-voltage gain to the high tube-voltage gain in synchronization with the second pulse that follows the first pulse. The period from the time when the DAS gain is switched to the starting time of the next view is used for stabilization of the A/D converter 522 for high tube voltage.

The second pulse may be either a pulse following the first pulse or a pulse following several pulses provided that it is a pulse output in the same view.

As shown in FIG. 5, sequential charge (integration) and read operations are performed on the X-ray detector 12 by the read control circuitry 512 in synchronization with the VT signal. More specifically, in the stable period of the high tube voltage or the low tube voltage, the read switches 122 are closed and the charge is performed by the X-ray detection elements 121. Charge is performed over the time length corresponding to a period of approximately 1 view, with the time of commencing charge shifted for each X-ray detection element row or each set of a predetermined number of rows. Electric signals are read from the X-ray detection elements 121 in order from an X-ray detection element row that has completed the charge. In a period T51 from the time when the charge is completed to the time when a predetermined time elapses, the read switches 122 are opened and electric signals are read from the X-ray detection elements 121. In a period T52 from the time when the period T51 ends to the time when a predetermined time passes, a read operation for drift-corrected data is performed. It is assumed that in the period T52 electric signals are not stored in the X-ray detection elements 121. With no charge, drift-corrected data is read from the X-ray detection elements 121.

As described above, the read operation is started for each X-ray detection element row 124 with the time shifted within the same view. The electric signals stored by X-ray irradiation in the first view are read in the following second view. As shown in FIG. 5, as the delay in reading electric signals is increased from the first row to the N-th row, the read operation is performed across the second view and the third view in the second and subsequent X-ray detection element rows.

After completion of electric signal reading, the electric signals are converted into digital data at an already-set DAS gain by the A/D converter 522 for high tube voltage or the A/D converter 523 for low tube voltage. Specifically, since the DAS gain is set to a high-tube-voltage gain in the period of applying a high tube voltage, electric signals are supplied from the X-ray detection elements 121 to the A/D converter 522 for high tube voltage and converted into projection data at a high-tube-voltage gain. Since the DAS gain is set to a low tube-voltage gain in the period of applying a low tube voltage, electric signals are supplied from the X-ray detection elements 121 to the A/D converter 523 for low tube voltage and converted into projection data at a low-tube-voltage gain.

Here, a difference between the embodiment described above and a comparative example will be described. The comparative example is a method in which gain switch instruction and data acquisition by A/D converter circuitry are performed in synchronization with the VT signal.

Figure 6:
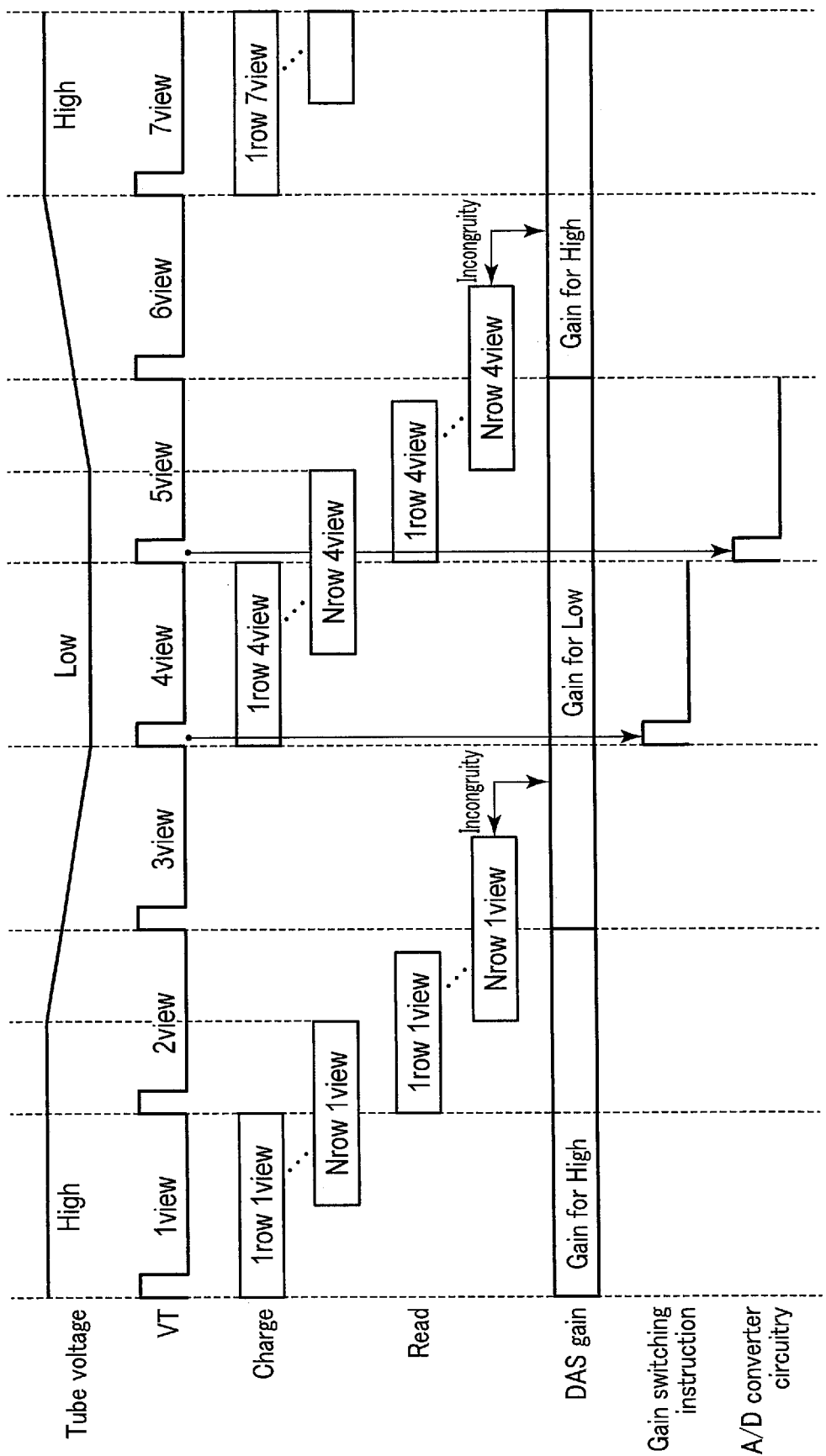
FIG. 6 is a diagram showing an example of a timing chart relating to the switching between a high tube voltage gain and a low tube voltage gain according to a comparative example.

FIG. 6 is a diagram showing an example of a timing chart relating to the switching between a high tube voltage gain and a low tube voltage gain according to the comparative example. In the comparative example as well, the stable period and the transitional period are set to 1.5 view in the same manner as shown in FIG. 5.

According to the comparative example, gain switch instruction and data acquisition by A/D converter circuitry are performed in synchronization with the VT signal, as shown in FIG. 6. For example, even if gain switch instruction is performed in synchronization with the VT signal in the fourth view, no further VT signal is output in the view; thus, it is impossible to perform data acquisition with the A/D converter circuitry. Data acquisition is eventually performed in synchronization with the VT signal output in the next fifth view. In the first row, all the electric charge stored upon application of a low tube voltage in the fourth view are read at a low-tube-voltage gain in the fifth view. However, in the second and subsequent X-ray detection element rows, such as the N-th rows, electric signals are read across the fifth view and the sixth view. However, since the DAS gain is switched to a high-tube-voltage gain in the sixth view, the electric charge stored upon application of a low tube voltage are read at a high-tube-voltage gain. That is, in the comparative example, a tube voltage relating to the time of charge and a tube voltage relating to the DAS gain do not coincide with each other in the X-ray detection element rows in which the read operation is performed across the views. Due to this incongruity, data acquisition is performed at a high-tube-voltage gain for the electric signals stored upon application of a low tube voltage, and data acquisition is performed at a low-tube-voltage gain for the electric signals stored upon application of a high tube voltage, making it impossible to perform data acquisition at a suitable gain. If there is a stable period in two or more views, data acquisition is performed at both a high-tube-voltage gain and a low-tube-voltage gain for the same tube voltage, causing deterioration of projection data quality.

According to the embodiment, even in the X-ray detection element rows in which the read operation is performed across the views, a tube voltage relating to the time of charge and a tube voltage relating to the DAS gain coincide with each other, as shown in FIG. 5. Thus, it is possible to switch DAS gains in synchronization with the kV switching. As a result, it is possible to perform data acquisition at a high-tube-voltage gain in a high-tube-voltage view and perform data acquisition at a low-tube-voltage gain in a low-tube-voltage view, thus making it possible to perform data acquisition at a suitable DAS gain for both a high tube voltage and a low tube voltage.

Next, acquisition of drift-corrected data will be described. The data acquisition circuitry 18 acquires drift-corrected data at high-tube-voltage gain and a second drift-corrected data at low-tube-voltage gain within the time of scanning a subject.

Figure 7:
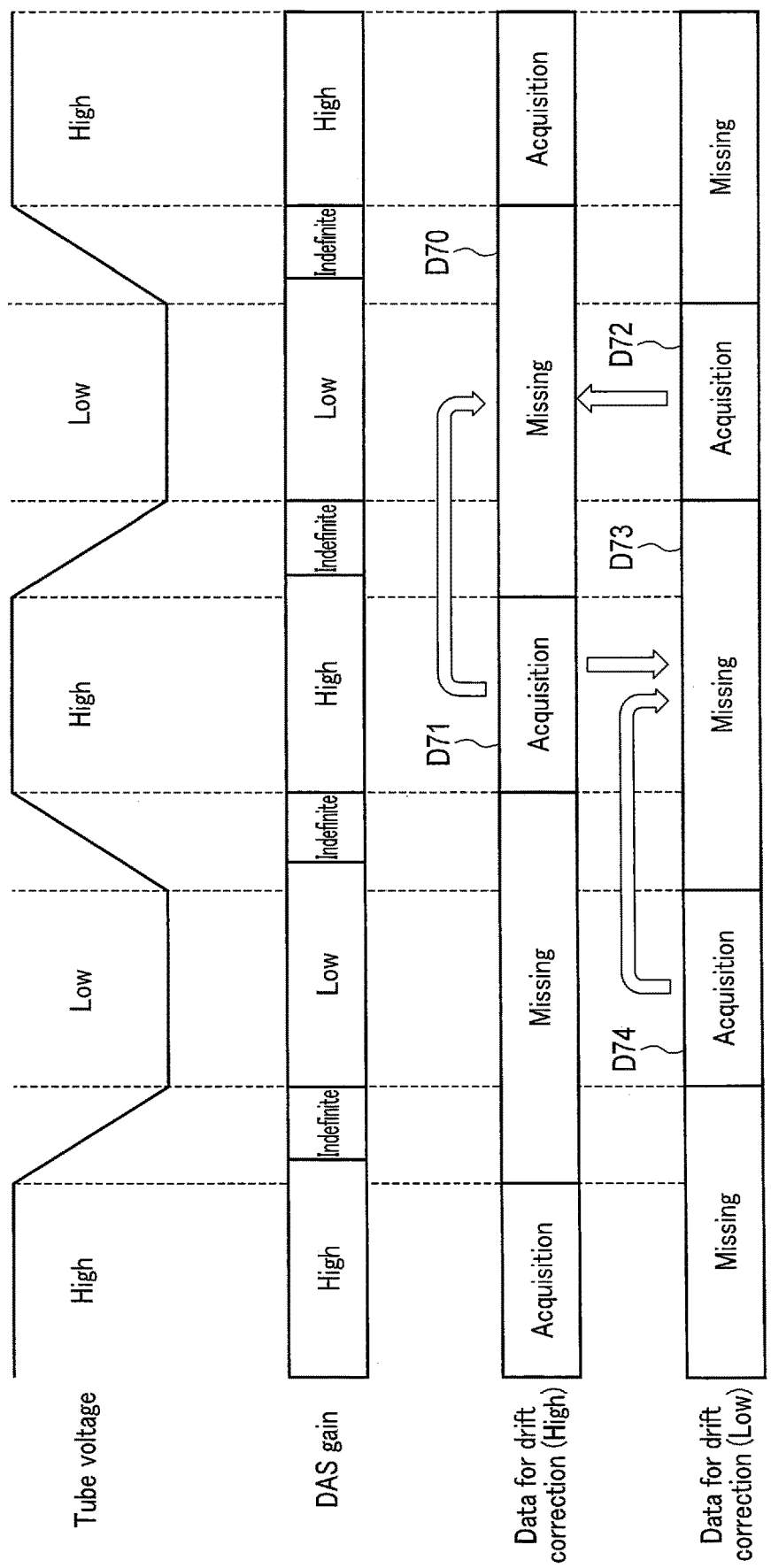
FIG. 7 is a timing chart relating to the acquisition of drift-corrected data.

FIG. 7 is a timing chart relating to acquisition of drift-corrected data. As shown in FIG. 7, the tube voltage is alternately switched between a high tube voltage (High) and a low tube voltage (Low) by the tube voltage control circuitry 141. Also, the DAS gain is alternately switched between a gain for high tube voltage (High) and a gain for low tube voltage (Low) by the gain switching control circuitry 514 in synchronization with switching of the tube voltage, as described above. In the transitional period of the tube voltage, none of the DAS gains is set.

The A/D converter circuitry 52 acquires digital data output from the A/D converter 522 in a first view (high-tube-voltage view) corresponding to the time of applying a high tube voltage while the read switches 122 are closed, as projection data at a first DAS gain (high-tube-voltage gain), and acquires digital data output from the A/D converter 522 after the projection data is acquired and while the read switches 122 are open, as first drift-corrected data (drift-corrected data for high tube voltage) at a high-tube-voltage gain. Also, the A/D converter circuitry 52 acquires digital data output from the A/D converter 523 in a second view (low-tube-voltage view) corresponding to the time of applying a low tube voltage while the read switches 122 are closed, as projection data at a low-tube-voltage gain, and acquires digital data output from the A/D converter 523 after the projection data is acquired and while the read switches 122 are open, as second drift-corrected data (drift-corrected data for low tube voltage) at a low-tube-voltage gain. Thus, the drift-corrected data for high tube voltage is missing at the time at which a low tube voltage is applied and in the transitional period, and the drift-corrected data for low tube voltage is missing at the time at which a high tube voltage is applied and in the transitional period.

As shown in FIG. 7, the computing circuitry 531 generates drift-corrected data D70 at high-tube-voltage gain that is missing in the low-tube-voltage view based on drift-corrected data D71 at high-tube-voltage gain acquired in the high-tube-voltage view before the low-tube-voltage view and/or drift-corrected data D72 at low-tube-voltage gain acquired in the same low-tube-voltage view. Likewise, the computing circuitry 531 generates drift-corrected data D73 at low-tube-voltage gain that is missing in the high-tube-voltage view based on drift-corrected data D74 at low-tube-voltage gain acquired in the low-tube-voltage view before the high-tube-voltage view and/or drift-corrected data D71 at high-tube-voltage gain acquired in the same high-tube-voltage view. The drift-corrected data generated based on already-acquired drift-corrected data will be referred to as "computational drift-corrected data". The computational drift-corrected data can be generated by various methods. Several generation methods will be described below.

(Method 1) The computing circuitry 531 computes the computational drift-corrected data D70 at high-tube-voltage gain corresponding to multiple views in a period from a certain high-tube-voltage view to the next high-tube-voltage view, based on the immediately preceding measured drift-corrected data D71 for high tube voltage acquired at a high-tube-voltage gain. Specifically, by considering that the drift-corrected data for high tube voltage in the low-tube-voltage view (stable period) becomes a repetition of the measured drift-corrected data for high tube voltage in the immediately preceding high-tube-voltage view (stable period), a moving average of the measured drift-corrected data for high tube voltage is set to the drift-corrected data for high tube voltage in the low-tube-voltage view (stable period). The drift-corrected data for high tube voltage in the transitional period immediately before and immediately after the low-tube-voltage view (stable period) may be set to a moving average of the measured drift-corrected data for high tube voltage in the immediately preceding high-tube-voltage view (stable period), or the moving average may be appropriately corrected to perform computation. The missing part of the drift-corrected data at low-tube-voltage gain can also be generated in a similar manner.

(Method 2) The computing circuitry 531 computes the drift-corrected data D70 at high-tube-voltage gain corresponding to multiple views in a period from a certain high-tube-voltage view to the next high-tube-voltage view, based on the measured drift-corrected data D72 for low tube voltage in the multiple views. Specifically, the behavioral tendency of the measured drift-corrected data D72 for low tube voltage in the multiple views is analyzed to calculate a correction value, the correction value is applied to the drift-corrected data D71 in the immediately preceding high-tube-voltage view, and the computational drift-corrected data D70 for high tube voltage is computed. The missing part of the drift-corrected data at low-tube-voltage gain can also be generated in a similar manner.

(Method 3) The computing circuitry 531 computes the drift-corrected data D70 at high-tube-voltage gain corresponding to multiple views in a period from a certain high-tube-voltage view to the next high-tube-voltage view, based on the measured drift-corrected data D72 for low tube voltage in the multiple views. Specifically, the computational drift-corrected data D70 for high tube voltage is computed by applying a bias so that the measured drift-corrected data D70 for low tube voltage in the multiple views matches an average value of the immediately preceding drift-corrected data D71 at high-tube-voltage gain. The missing part of the drift-corrected data at low-tube-voltage gain can also be generated in a similar manner.

(Method 4) The computing circuitry 531 generates a missing part of the drift-corrected data using a machine-trained model. To give an example, a machine-trained model can be used that is trained so that drift-corrected data at high-tube-voltage gain in a first view is input and drift-corrected data at high-tube-voltage gain in the second view that follows the first view is output. In this case, the computing circuitry 531 can apply the measured drift-corrected data at high-tube-voltage gain in the high-tube-voltage view to the machine-trained model and generate the computational drift-corrected data at high-tube-voltage gain in the low-tube-voltage view that follows the high-tube-voltage view. The missing part of the drift-corrected data at low-tube-voltage gain can also be generated in a similar manner. To give another example, a machine-trained model can be used that is trained so that drift-corrected data at low-tube-voltage gain in the first view is input and drift-corrected data at high-tube-voltage gain in the first view is output. In this case, the computing circuitry 531 can apply the measured drift-corrected data at low-tube-voltage gain in the low-tube-voltage view to the machine-trained model and generate the computational drift-corrected data at high-tube-voltage gain in the low-tube-voltage view. The missing part of the drift-corrected data at low-tube-voltage gain can also be generated in a similar manner.

(Method 5) The computing circuitry 531 may generate the missing part of the drift-corrected data at high-tube-voltage gain by correcting the immediately preceding measured drift-corrected data at high-tube-voltage gain based on the temperature data of the X-ray detector 12 and/or the device(s) in the data acquisition circuitry 18. For the X-ray detector 12 and/or the device(s) in the data acquisition circuitry 18, temperature data is measured by a temperature-measuring device. It is possible to analyze the temperature fluctuation of the devices in a view preceding a view corresponding to the missing part and generate computational drift-corrected data for high tube voltage based on the temperature fluctuation. The missing part of the drift-corrected data at low-tube-voltage gain can also be generated in a similar manner.

The measured or computational drift-corrected data generated by the above method is stored in the corrected data storage device 532 in such a manner that it is associated with its corresponding type of DAS gain and view number. According to the embodiment, it is possible to acquire drift-corrected data at high-tube-voltage gain and a drift-corrected data at low-tube-voltage gain. Also, interpolating the missing part by the above method renders it possible to acquire drift-corrected data at high-tube-voltage gain and drift-corrected data at low-tube-voltage gain throughout the views.

Next, the acquisition of offset-corrected data will be described. The data acquisition circuitry 18 acquires first offset-corrected data corresponding to high-tube-voltage gain and second offset-corrected data corresponding to low-tube-voltage gain.

Figure 8:
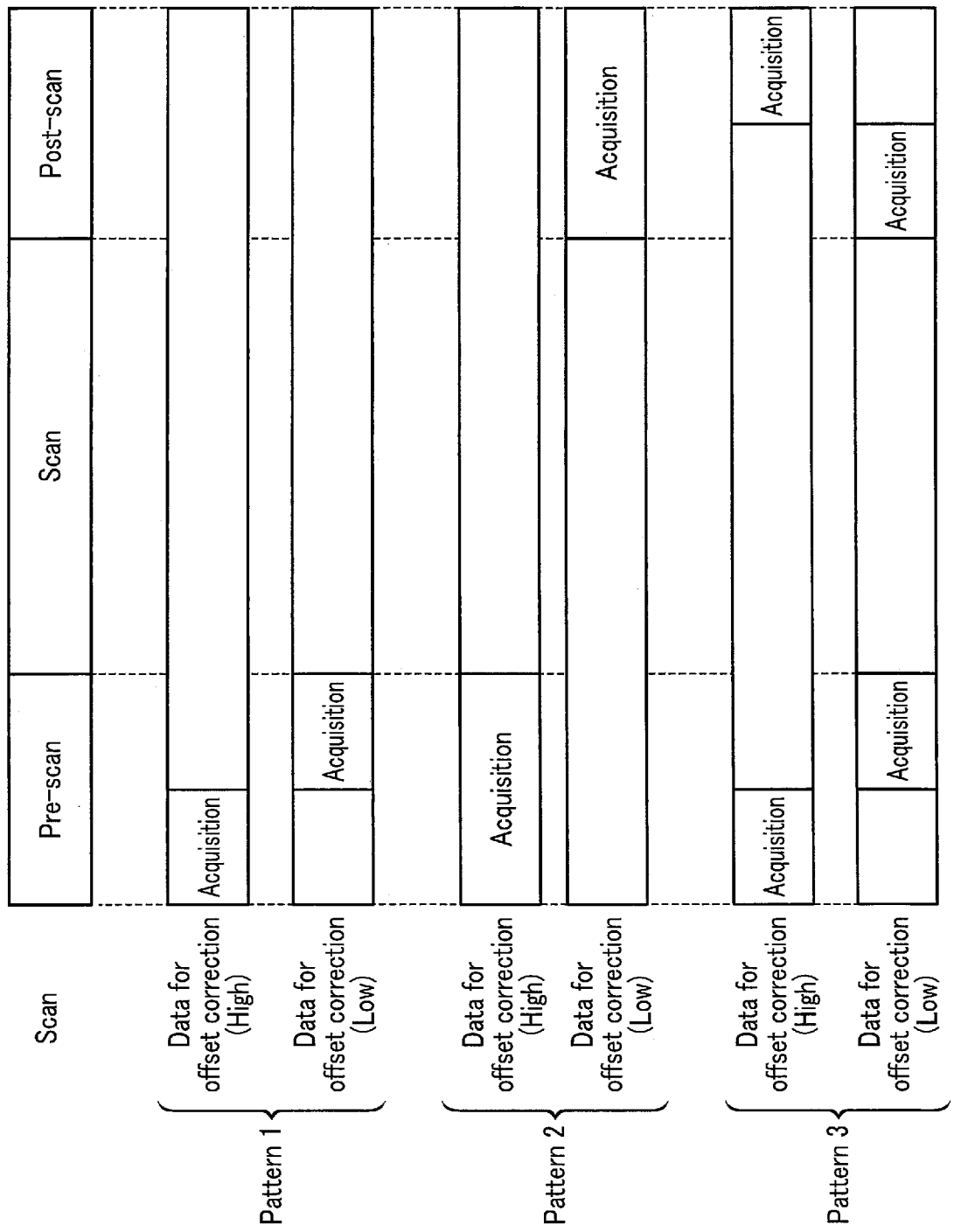
FIG. 8 is a timing chart relating to the acquisition of offset-corrected data.

FIG. 8 is a timing chart relating to acquisition of offset-corrected data. As shown in FIG. 8, a CT examination has a pre-scan stage, a scan stage, and a post-scan stage. In the scan stage, dual energy scan through kV switching is performed, as described above. Before the scan and/or after the scan, offset-corrected data at high-tube-voltage gain and offset-corrected data at low-tube-voltage gain are acquired by the data acquisition circuitry 18. At the time when a high tube voltage is applied, the data acquisition circuitry 18 acquires, as offset-corrected data at high-tube-voltage gain, digital data output from the A/D converter 522 while the read switches 122 are closed or open; and at the time when a low tube voltage is applied, the data acquisition circuitry 18 acquires, as offset-corrected data at low-tube-voltage gain, digital data output from the A/D converter 523 while the read switches 122 are closed or open. The offset-corrected data at each DAS gain need not be acquired in all the views covering 360 degrees and may be acquired in any view. The acquired offset-corrected data at each DAS gain can be used for both the views in which the data is acquired and the views in which the data is not acquired.

The method of acquiring offset-corrected data can have roughly three patterns.

In pattern 1, both offset-corrected data at high-tube-voltage gain and offset-corrected data at low-tube-voltage gain are acquired before the scan, as shown in FIG. 8. The manner of acquiring offset-corrected data may be either of the following: acquire offset-corrected data at high-tube-voltage gain first and then acquire offset-corrected data at low-tube-voltage gain; or acquire offset-corrected data at low-tube-voltage gain first and then acquire offset-corrected data at high-tube-voltage gain.

In pattern 2, offset-corrected data at high-tube-voltage gain is acquired before the scan, and offset-corrected data at low-tube-voltage gain is acquired after the scan, as shown in FIG. 8. In contrast, offset-corrected data at low-tube-voltage gain may be acquired before the scan, and offset-corrected data at high-tube-voltage gain may be acquired after the scan.

In pattern 3, both offset-corrected data at high-tube-voltage gain and offset-corrected data at low-tube-voltage gain are acquired both before the scan and after the scan, as shown in FIG. 8. For example, offset-corrected data at high-tube-voltage gain is acquired prior to offset-corrected data at low-tube-voltage gain before the scan, and offset-corrected data at low-tube-voltage gain is acquired prior to offset-corrected data at high-tube-voltage gain after the scan. The order of acquiring offset-corrected data at high-tube-voltage gain and offset-corrected data at low-tube-voltage gain in each of before the scan and after the scan is not particularly limited.

Measured or computational offset-corrected data generated by the above method is stored in the corrected data storage device 532. According to the embodiment, it is possible to acquire offset-corrected data at high-tube-voltage gain and offset-corrected data at low-tube-voltage gain.

Second Embodiment

Figure 9:
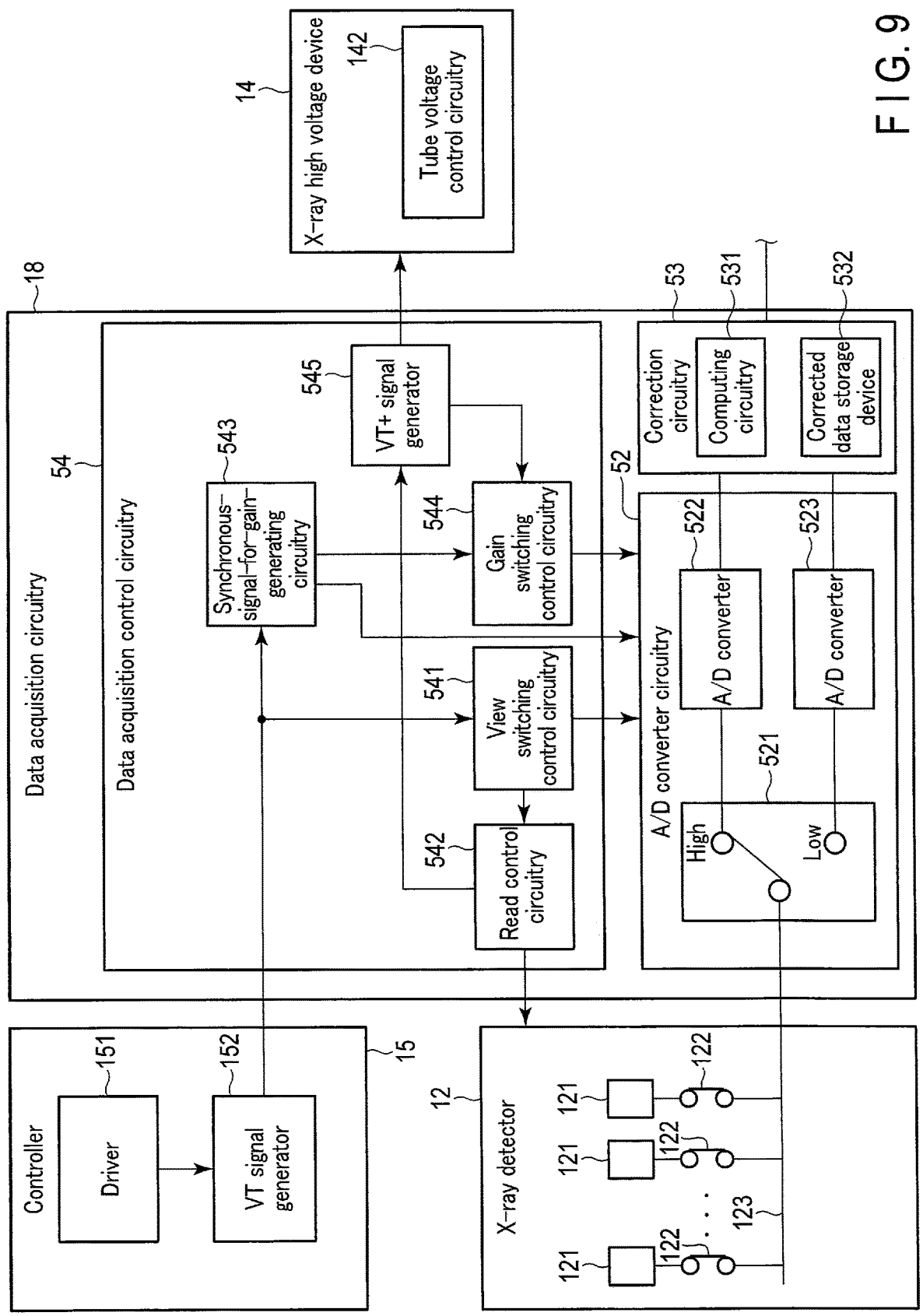
FIG. 9 is a diagram showing an example of configurations of main components relating to kV switching according to a second embodiment.

FIG. 9 is a diagram showing an example of configurations of main components relating to kV switching according to a second embodiment. In the description provided below, constituents having substantially the same functions as those of the first embodiment will be denoted by the same reference symbols as those used in the first embodiment, and a repeat description will be given only where necessary.

As shown in FIG. 9, an X-ray computed tomography apparatus 1 according to the second embodiment includes an X-ray detector 12, an X-ray high voltage device 14, a controller 15, and data acquisition circuitry 18 as main components relating to kV switching. Data acquisition control circuitry 54 of the data acquisition circuitry 18 includes a VT+ signal generator 545 in addition to view switching control circuitry 541, read control circuitry 542, synchronous-signal-for-gain-generating circuitry 543, and gain switching control circuitry 544.

The view switching control circuitry 541 switches views based on a VT signal from the VT signal generator 152 in the same manner as the view switching control circuitry 511 of the first embodiment.

In the same manner as the read control circuitry 512 of the first embodiment, the read control circuitry 542 controls both the opening and closing of each of the read switches 122 connected to each of the X-ray detection elements 121 in the sequential read method.

The synchronous-signal-for-gain-generating circuitry 543 generates a synchronous signal for gain in the same manner as that of the gain switching control circuitry 514 of the first embodiment.

The VT+ signal generator 545 generates a VT+ signal, which is a signal reporting that the reading of electric signals from all the X-ray detection element rows 124 is completed. As described above, for each of the X-ray detection element rows 124, the read control circuitry 542 supplies ON signals to the read switches 122 in the storage view, and supplies OFF signals to the read switches 122 in the read view. The VT+ signal generator 545 monitors the supply of OFF signals from the read control circuitry 542, and upon the supply of OFF signals to the read switches 122 for the X-ray detection element row 124 in the last row, generates a VT+ signal. The VT+ signal generator 545 may generate a VT+ signal with a delay of any time amount with respect to the time when OFF signals are supplied. The VT+ signal is supplied to tube voltage control circuitry 142 and the gain switching control circuitry 544.

The gain switching control circuitry 544 switches DAS gains based on the synchronous signal for gain and the VT+ signal. Specifically, the gain switching control circuitry 544 switches DAS gains between a high-tube-voltage gain and a low-tube-voltage gain at a timing when both the synchronous signal for gain and the VT+ signal are output (i.e., at a timing of AND of both the synchronous signal for gain and the VT+ signal). The plan for gain change relating to the question of whether to switch to a high-tube-voltage gain or low-tube-voltage gain is the same as that of the first embodiment. If the processing circuitry 44 transmits a gain switch instruction to the gain switching control circuitry 514, it may do so in synchronization with the VT+ signal. This allows the gain switching control circuitry 514 to notify the A/D converter circuitry 52 of the gain switch instruction in the next view where the VT+ signal is received.

The tube voltage control circuitry 142 according to the second embodiment switches tube voltages between a high tube voltage and a low tube voltage based not on the VT signal but on the VT+ signal. Switching tube voltages based on the VT+ signal renders it possible to perform the operation of switching tube voltages immediately after reading from all the X-ray detection element rows 124 is completed.

Figure 10:
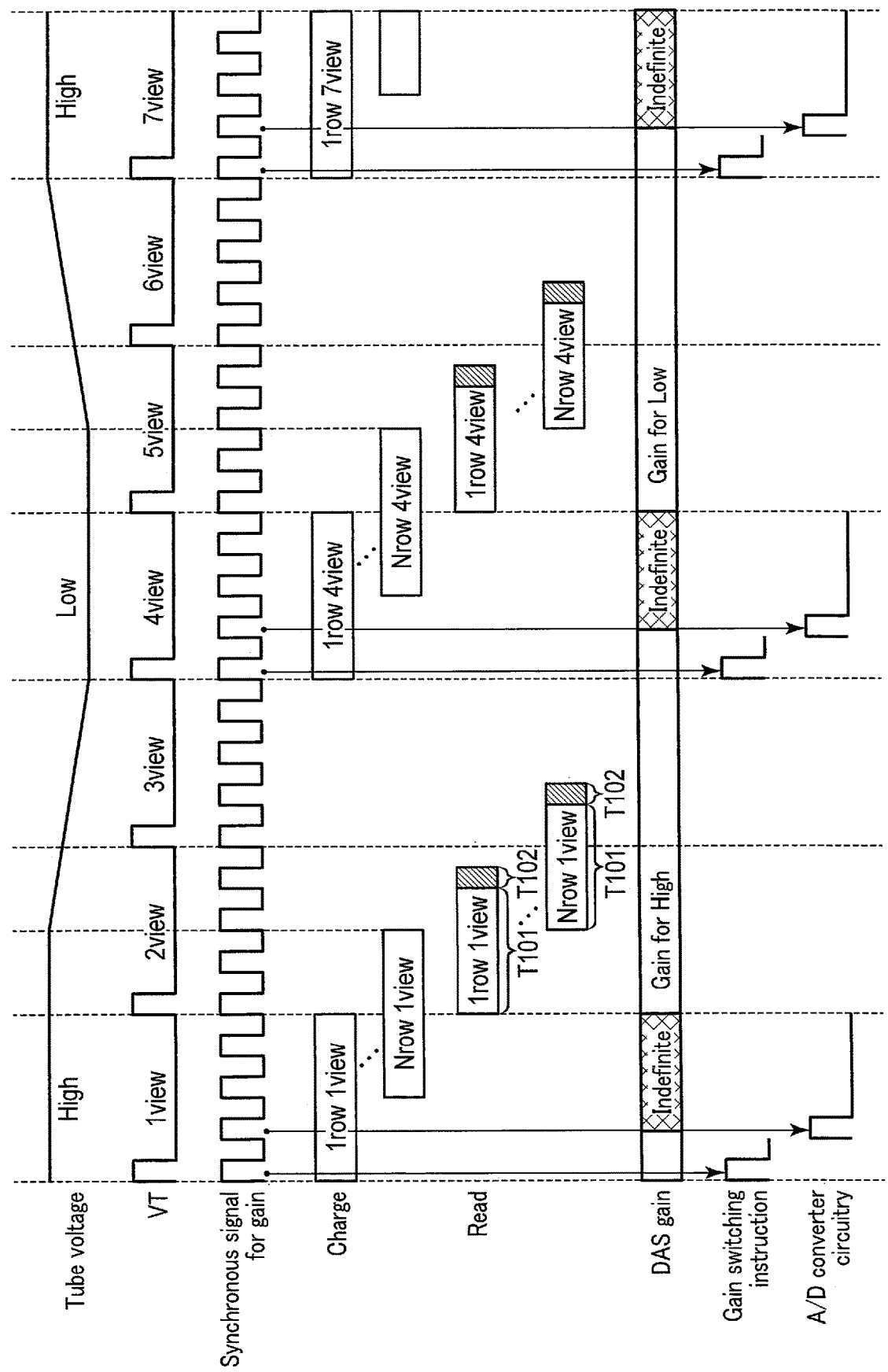
FIG. 10 is a diagram showing an example of a timing chart relating to the switching between a high tube voltage gain and a low tube voltage gain according to the second embodiment.

Next, switching between a high-tube-voltage gain and a low-tube-voltage gain according to the second embodiment will be described. FIG. 10 is a diagram showing an example of a timing chart relating to the switching between a high tube voltage gain and a low tube voltage gain according to the second embodiment.

As shown in FIG. 10, a VT signal is repeatedly output by the VT signal generator 152 at a fixed first time interval, and the view is switched by the view switching control circuitry 511 when the VT signal is output. The VT+ signal is output by the VT+ signal generator 545 at a timing when the signal reading in the last row is completed. The gain switching control circuitry 544 notifies the A/D converter circuitry 52 of a gain switch instruction in synchronization with the output of a first pulse of the synchronous signal for gain in the next view in which the VT+ signal is output. Then, the gain switching unit 521 of the A/D converter circuitry 52 switches DAS gains in synchronization with the output of a second pulse following the first pulse. The second pulse may be a pulse output adjacent to the first pulse or a pulse output after several pulses. Thus, a tube voltage relating to the time of charge and a tube voltage relating to the DAS gain coincide with each other, as in the case of the first embodiment.

In the second embodiment as well, sequential charge (integration) and read operations are performed on the X-ray detector 12 by the read control circuitry 512 in synchronization with the VT signal, as in the first embodiment shown in FIG. 5. More specifically, in the view of the stable period of the high tube voltage or the low tube voltage, the read switches 122 are closed and charge is performed by the X-ray detection elements 121. Charge is performed over the time length corresponding to a period of approximately 1 view with the time of commencing charge shifted for each X-ray detection element row or each set of a predetermined number of rows. Electric signals are read from the X-ray detection elements 121 in order from an X-ray detection element row that has completed the charge. In a period T101 from the time when the charge is completed to the time when a predetermined time elapses, the read switches 122 are opened and electric signals are read from the X-ray detection elements 121. In a period T102 from the time when the period T101 ends to the time when a predetermined time elapses, a read operation for drift-corrected data is performed.

As described above, according to the second embodiment, the switching of tube voltages and switching of DAS gains are performed in synchronization with the VT+ signal, thus allowing for switching of DAS gains in synchronization with kV switching.

According to at least one embodiment described above, gains relating to data acquisition can be switched in synchronization with switching of tube voltages.

The term "processor" used in the above description means, for example, circuitry such as a CPU, a GPU, an application specific integrated circuit (ASIC), or a programmable logic device (e.g., a simple programmable logic device (SPLD), a complex programmable logic device (CPLD), or a field programmable gate array (FPGA)). The processor implements a function by reading and executing a program stored in storage circuitry. Instead of storing a program in storage circuitry, the program may be directly incorporated into processor circuitry. In this case, the processor reads and executes the program integrated into the circuitry to realize its functions. The functions corresponding to the program may be realized not by executing the program but by a combination of logic circuits. Each processor of the present embodiment is not limited to a configuration as a single circuit; a plurality of independent circuits may be combined into one processor to realize its functions. Besides, the structural elements in FIG. 1, FIG. 2 and FIG. 9 may be integrated into a single processor, and the processor may implement the functions of the structural elements.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
   tube voltage control circuitry configured to switch a tube voltage applied to an X-ray tube between a first tube voltage and a second tube voltage lower than the first tube voltage;
   VT signal generating circuitry configured to generate a VT signal at a first time interval;
   view switching control circuitry configured to switch a view based on the generated VT signal;
   A/D converter circuitry configured to perform data acquisition in units of views through an X-ray detector;
   synchronous-signal-for-gain-generating circuitry configured to generate a synchronous signal at a second time interval shorter than the first time interval; and
   gain switching control circuitry configured to switch a gain of the A/D converter circuitry based on the synchronous signal.

2. The X-ray computed tomography apparatus according to claim 1, wherein the gain switching control circuitry is further configured to switch the gain between a first gain corresponding to the first tube voltage and a second gain corresponding to the second tube voltage based on the second switch signal.

3. The X-ray computed tomography apparatus according to claim 2, wherein the gain switching control circuitry is further configured to switch between the first gain and the second gain so as to match a tube voltage corresponding to the data acquired through the X-ray detector.

4. The X-ray computed tomography apparatus according to claim 3, wherein the A/D converter circuitry is further configured to acquire, within a time of scanning a subject, first drift-corrected data corresponding to the first gain and second drift-corrected data corresponding to the second gain.

5. The X-ray computed tomography apparatus according to claim 4, wherein
   the X-ray detector includes an X-ray detection element and a read switch of the X-ray detection element,
   the A/D converter circuitry is connected to the X-ray detection element via the read switch and includes an A/D converter (ADC) configured to convert an electric signal into digital data, and
   the A/D converter circuitry is configured to:
      acquire the digital data as projection data in a first view corresponding to a time of applying the first tube voltage, the digital data being output from the ADC while the read switch is closed; and acquire the digital data as the first drift-corrected data in the first view, the digital data being output from the ADC after the projection data is acquired and while the read switch is open; and
      acquire the digital data as the projection data in a second view corresponding to a time of applying the second tube voltage, the digital data being output from the ADC while the read switch is closed; and acquire the digital data as the second drift-corrected data in the second view, the digital data being output from the A/D converter after the projection data is acquired and while the read switch is open.

6. The X-ray computed tomography apparatus according to claim 5, wherein
   the A/D converter circuitry is further configured to:
      generate the second drift-corrected data that is missing in the first view based on the first drift-corrected data acquired in the first view and/or the second drift-corrected data acquired in the second view; and
      generate the first drift-corrected data that is missing in the second view based on the second drift-corrected data acquired in the second view and/or the first drift-corrected data acquired in the first view.

7. The X-ray computed tomography apparatus according to claim 5, wherein the A/D converter circuitry is further configured to generate the second drift-corrected data that is missing in the first view by correcting the first drift-corrected data acquired in the first view and/or the second drift-corrected data acquired in the second view using temperature data of the data acquisition circuitry measured in the first view.

8. The X-ray computed tomography apparatus according to claim 3, wherein the A/D converter circuitry is further configured to acquire, outside a time of scanning a subject, first offset-corrected data corresponding to the first gain and second offset-corrected data corresponding to the second gain.

9. The X-ray computed tomography apparatus according to claim 8, wherein
   the X-ray detector includes an X-ray detection element and a read switch of the X-ray detection element,
   the A/D converter circuitry is connected to the X-ray detection element via the read switch and includes an A/D converter (ADC) configured to convert an electric signal into digital data, and
   the A/D converter circuitry is further configured to:
      acquire the digital data as the first offset-corrected data at a time of applying the first tube voltage, the digital data being output from the (ADC) while the read switch is closed; and
      acquire the digital data as the second offset-corrected data at a time of applying the second tube voltage, the digital data being output from the ADC while the read switch is closed.

10. The X-ray computed tomography apparatus according to claim 9, wherein
    the A/D converter circuitry is configured to:
       acquire the first offset-corrected data and the second offset-corrected data before scanning;
       acquire the first offset-corrected data before scanning and acquire the second offset-corrected data after scanning;
       acquire the second offset-corrected data before scanning and acquire the first offset-corrected data after scanning; or
       acquire the digital data at the first gain and the digital data at the second gain both before scanning and after scanning, generate the first offset-corrected data based on the digital data at the first gain before scanning and after scanning, and generate the second offset-corrected data based on the digital data at the second gain before scanning and after scanning.

11. The X-ray computed tomography apparatus according to claim 1, wherein the synchronous-signal-for-gain-generating circuitry is further configured to upsample the first switch signal and generate the second switch signal synchronized with the first switch signal.

12. The X-ray computed tomography apparatus according to claim 1, wherein
    the synchronous-signal-for-gain-generating circuitry is further configured to generate a first pulse and a second pulse following the first pulse as the second switch signal at the first time interval, the gain switching control circuitry is further configured to provide a switch instruction to the A/D converter circuitry in synchronization with the first pulse, and the A/D converter circuitry is further configured to switch to a gain corresponding to the switch instruction in synchronization with the second pulse.

13. The X-ray computed tomography apparatus according to claim 1, wherein the gain switching control circuitry is further configured to switch the gain of the A/D converter circuitry based on the second switch signal and a third switch signal that is generated at a timing at which reading of electric charge from all detection element rows of the X-ray detector is completed.

* * * * *